United States Patent [19]

Ternansky

[11] Patent Number: 5,247,073
[45] Date of Patent: Sep. 21, 1993

[54] 7-(AMINO OR PROTECTED AMINO)-3-THIOHETEROBICYCLIC CEPHALOSPORINS

[75] Inventor: Robert J. Ternansky, Indianapolis, Ind.

[73] Assignee: Eli Lilly and Company, Indianapolis, Ind.

[21] Appl. No.: 907,885

[22] Filed: Jul. 2, 1992

Related U.S. Application Data

[62] Division of Ser. No. 642,959, Jan. 18, 1991, abandoned.

[51] Int. Cl.$^5$ ............................................ C07D 498/053
[52] U.S. Cl. .................................... 540/225; 540/226; 540/227
[58] Field of Search ..................... 540/226, 227, 225

[56] References Cited

U.S. PATENT DOCUMENTS

| | | | |
|---|---|---|---|
| 4,123,528 | 10/1978 | Cama et al. | 424/248.52 |
| 4,500,526 | 2/1985 | Imae et al. | 514/226 |
| 5,142,039 | 8/1992 | Blaszczak et al. | 540/226 |

FOREIGN PATENT DOCUMENTS

| | | |
|---|---|---|
| 160564 | 11/1985 | European Pat. Off. |
| 182301 | 5/1986 | European Pat. Off. |
| 1-272590 | 10/1989 | Japan |
| WO91/09037 | 6/1991 | Japan |
| 794749 | 9/1979 | South Africa |
| 1533795 | 7/1976 | United Kingdom |
| 2177691 | 1/1987 | United Kingdom |

OTHER PUBLICATIONS

Shintaro Nishimura et al., "Synthesis and Biological Activity of 3-vinylthio-and 3-vinylthiomethylcephem Derivatives", *The Journal of Antibiotics*, vol. XLIII, No. 9, pp. 1160-1168 (Sep. 1990).

*Primary Examiner*—Nicholas S. Rizzo
*Attorney, Agent, or Firm*—James J. Sales; Leroy Whitaker

[57] ABSTRACT

The present invention provides compounds of the formula

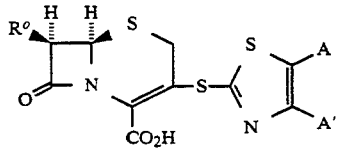

wherein $R^0$ is amino or protected amino; A and A' are taken together form a group of the formulae

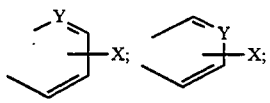

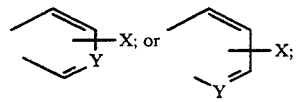

wherein X is hydrogen, halo, $C_1$-$C_6$ alkyl, $C_1$-$C_6$ alkoxy, $C_1$-$C_6$ alkoxycarbonyl, amino, nitro, carboxy; and Y is nitrogen; or a pharmaceutically acceptable salt thereof.

2 Claims, No Drawings

7-(AMINO OR PROTECTED AMINO)-3-THIOHETEROBICYCLIC CEPHALOSPORINS

This application is a division of application Ser. No. 07/642,959, filed Jan. 18, 1991 now abandoned.

BACKGROUND OF THE INVENTION

This invention relates to cephalosporin antibiotics, to pharmaceutical formulations comprising the antibiotics, and to a method for the treatment of infectious diseases in man and other animals.

Cephalosporin antibiotics have the bicyclic ring system represented by the following formula wherein the numbering system is that commonly employed in the arbitrary cepham nomenclature system.

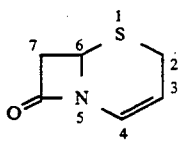

In the field of antibacterial therapy, the need for new chemotherapeutic agents is one that will never extinguish. Mutant strains resistant to existing antibacterial agents are encountered frequently. In particular, many strains of Staph. aureus and Staph. epi (so-called methicillin resistant Staph. (MRS)) are becoming increasingly resistant to available antibacterial agents. (see, for example, Phillips, I., and Cookson, B., J. Appl. Bacteriology 67(6)1989). To meet this need, considerable research effort continues to focus on such new agents. The present invention provides antibacterial agents useful against a wide variety of gram-positive and gram-negative bacteria. The compounds of the present invention are especially useful against these methicillin-resistant Staph. organisms.

SUMMARY OF THE INVENTION

The present invention provides various 3-thiazolothio cephalosporins useful as antibacterial agents. In particular, the present invention provides 7β-(2-aminothiazol-4-yl)oximino-(or alkoximino)acetylamino-3-optionally-substituted-thiazolothio-3-cephem-4-carboxylic acids useful as antibacterial agents. The invention also provides pharmaceutical formulations and a therapeutic method useful in the treatment of antibacterial infections in man and other animals.

DETAILED DESCRIPTION OF THE INVENTION

The present invention provides compounds of Formula (1):

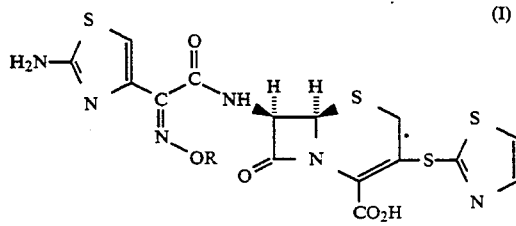

wherein R is hydrogen, $C_1$–$C_6$ alkyl, $C_2$–$C_6$ alkenyl, $C_2$–$C_6$ alkynyl, $C_3$–$C_6$ cycloalkyl, or $C_1$–$C_6$ haloalkyl; A and A' are independently hydrogen, $C_1$–$C_6$ alkyl, nitro, amino, $C_1$–$C_6$ alkoxy, a 5 or 6 membered heterocycle containing nitrogen or sulfur, or phenyl; or A and A' taken together form a group of the formulae

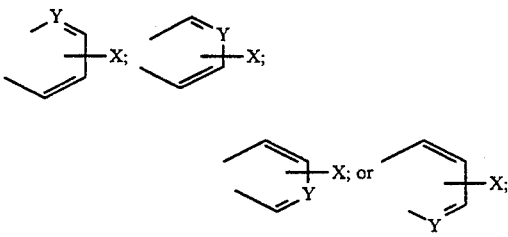

wherein X is hydrogen, halo, $C_1$–$C_6$ alkyl, $C_1$–$C_6$ alkoxy, $C_1$–$C_6$ alkoxycarbonyl, amino, nitro, or carboxy; and Y is nitrogen or carbon; or a pharmaceutically acceptable salt thereof.

The term "pharmaceutically-acceptable salt" encompasses those salts that form with the carboxylate anions and includes salts formed with the organic and inorganic cations such as counterions chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)-ammonium, phenylethylbenzylammonium, dibenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the compounds represented by formula (1) formed by a carboxylic acid and an amino group is referred to by this term. A preferred cation for the carboxylate anion is the sodium cation. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

In the above Formula (1), the term "$C_1$–$C_6$ alkyl" denotes such radicals as methyl, ethyl, n-propyl, isopropyl, n-butyl, sec-butyl, tert-butyl, amyl, tert-amyl, hexyl and the like. The preferred "$C_1$–$C_6$ alkyl" group is methyl.

The term "$C_2$–$C_6$ alkenyl" is a straight chain or branched lower alkenyl and is exemplified by vinyl, allyl, 1-propenyl, isopropenyl, 1-butenyl, 2-butenyl, 3-butenyl, methallyl, or 1,1-dimethylallyl.

The term "$C_2$–$C_6$ alkynyl" is a straight chain or branched lower alkynyl group and is exemplified by ethynyl, 1-propynyl, or propargyl.

The term "$C_3$–$C_{10}$ cycloalkyl" is exemplified by cyclopropyl, cyclobutyl, cyclopentyl, cyclohexyl, cycloheptyl, norbornyl or adamantayl.

The term "$C_1$–$C_6$ haloalkyl" denotes the above $C_1$–$C_6$ alkyl groups that are substituted by one halogen, wherein "halo" or "halogen" denotes the chloro, bromo, iodo, and fluoro groups. Fluoro $C_1$–$C_6$ alkyl is preferred. Fluoroethyl is a further preferred "$C_1$–$C_6$ haloalkyl" group.

The term "$C_1$–$C_6$ alkoxy" refers to such groups as methoxy, ethoxy, 3-propoxy, butyloxy, and the like.

The term "halo" includes fluoro, bromo, chloro and iodo.

The term "$C_1$–$C_6$ alkoxycarbonyl" refers to such groups as methoxycarbonyl, ethoxycarbonyl, 3-propoxycarbonyl, 3-ethoxycarbonyl, 4-t-butyloxycarbonyl, 3-methoxycarbonyl, 6-methoxycarbonyl, and the like.

The term "5 or 6 membered heterocycle containing nitrogen or sulfur" includes pyridine and thiophene, and may include more than a nitrogen or sulfur, and combinations thereof. Other examples include those described in Fletcher, Dermer, & Otis, *Nomenclature of Organic Compounds*, pp. 49–64 (1974), incorporated herein by reference.

Compounds of Formula (1) may be prepared according to Scheme 1:

(available from Aldrich Chemical Co., Inc., 940 West Saint Paul Avenue, Milwaukee, Wis. 53233) utilizing methodology well-known in the β-lactam art. Starting material (B), or benzhydryl 7-amino-3-trifluoromethanesulfonoxy-3-cephem-4-carboxylate may be prepared using known methodology, such as from the corresponding 3-enol-3-cepham and trifluoromethanesulfonoxyacetic anhydride. (*Syn. Commun.* 20(14), 2185–2189 (1990)

In Scheme 1, the acid chloride of (A) can be prepared by known methodology, for example, by reaction with phosphoryl chloride, and reacted with the free amine (B) to form the 7-acyl-3-triflate (C). The thiazolothio group can then be introduced by reacting the triflate (C) with a compound of formula

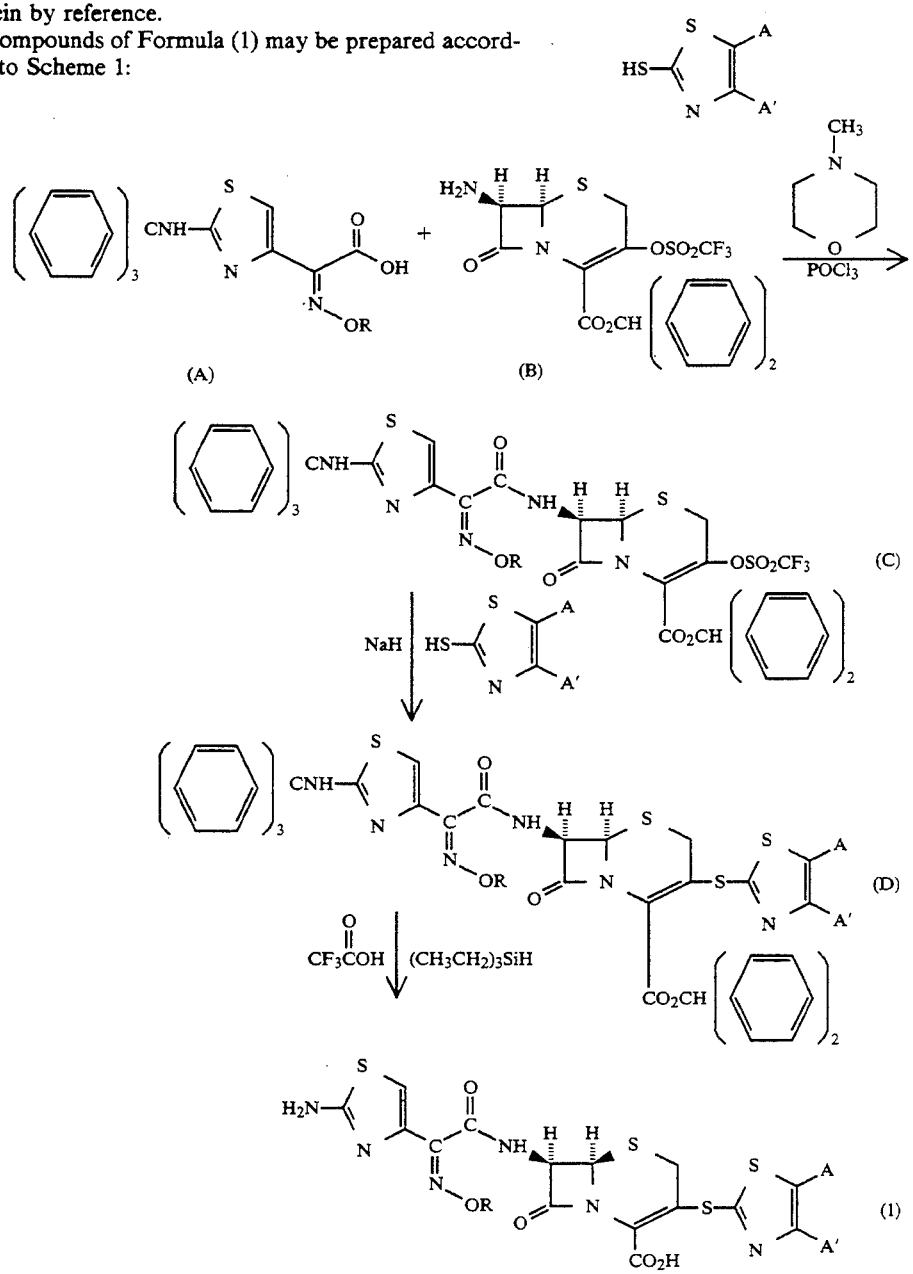

The starting material (A), (wherein R is methyl), 2-(trityl)amino-α-(methoxy-imino)-4-thiazoleacetic acid may be prepared from the corresponding free amine in the presence of a base such as NaH. The final product (1) can then be prepared by removal of amino and carboxy protecting groups. In the above scheme, $CF_3CO_2H/(CH_3CH_2)_3SiH$ is utilized to remove the trityl and benzhydryl groups. One of ordinary skill in the art of β-lactam chemistry will appreciate that other protecting groups wold be efficacious. Further, one may also introduce the thiazolothio function into the 3-position of the cephem nucleus (B) prior to the insertion of the 7-acyl functions to provide useful intermediates set forth in formula (2) below.

Alternatively, the compounds may be prepared according to Scheme (2) below:

diazomethane, and the thiazolothio group is introduced in the presence of a base such as NaH, to form compound (D). The removal of the benzhydryl and trityl groups may be removed as in Scheme (1).

Compounds of the formula 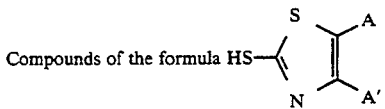

where A and A' are taken together to form a group of the formulae

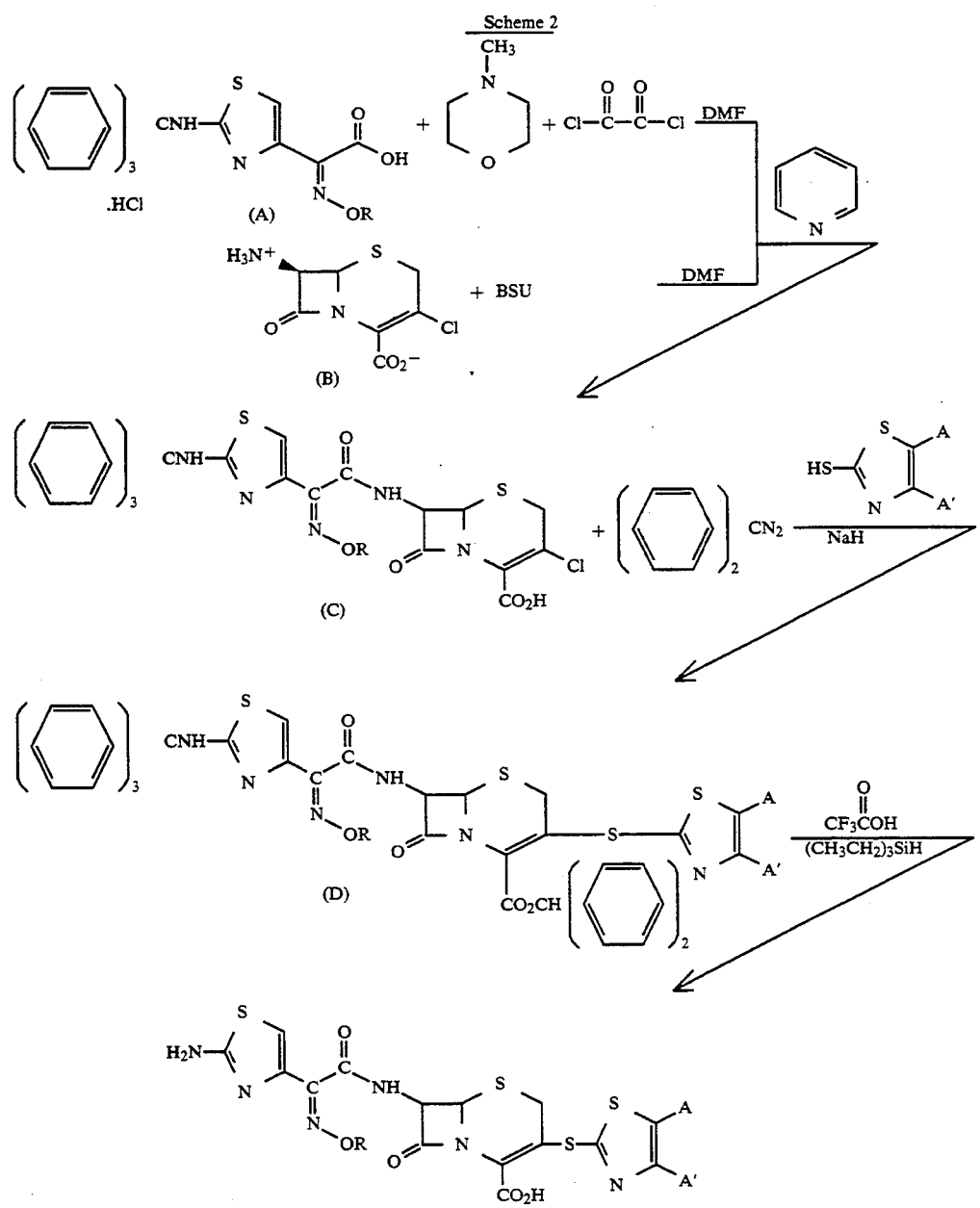

In Scheme (2), the acetic acid (A), dissolved in DMF, is treated with N-methylmorpholine and oxalyl chloride A mixture of 7β-amino-3-chloro-cephem dissolved in DMF and treated with bis(dimethylsilyl)urea (BSU) and pyridine is combined with the acetic acid, to form (C). Compound (C) is then treated with diphenyl-

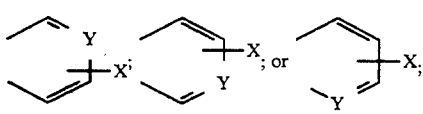

and Y is nitrogen may be prepared according to the Scheme (3):

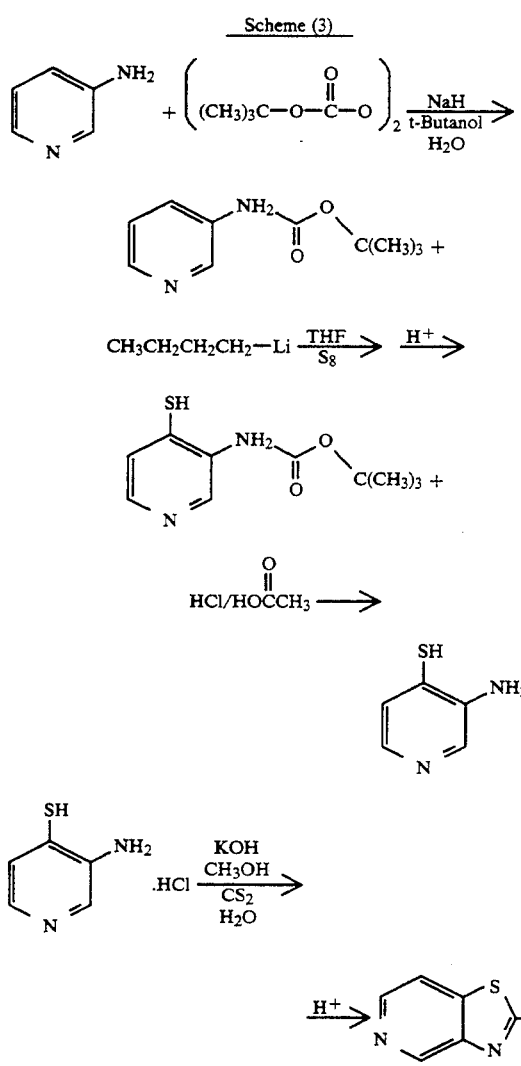

In Scheme (3), 3-aminopyridine is acylated with di-t-butyldicarbonate to introduce the t-butoxycarbonyl (t-BOC) protecting group. (It will be appreciated that two other pyridinothiazolothio mercaptans may be prepared by known methodology using other amino pyridine isomers.) The t-BOC protected 3-aminopyridine is then treated with n-butyllithium in tetrahydrofuran followed by elemental sulfur ($S_8$), followed by treatment with saturated ammonium chloride. The resulting 3-t-butoxycarbonylamino-4-thia-pyridine is treated with a mixture of acetic acid and HCl to provide 3-amino-4-mercaptopyridine hydrochloride. The desired 5-pyridinothiazolo thiomercaptan can then be prepared by treating this compound with carbon disulfide under basic conditions.

When A and A' are taken together to form a group of the formula

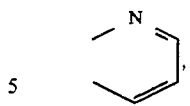

the desired thiol of the formula

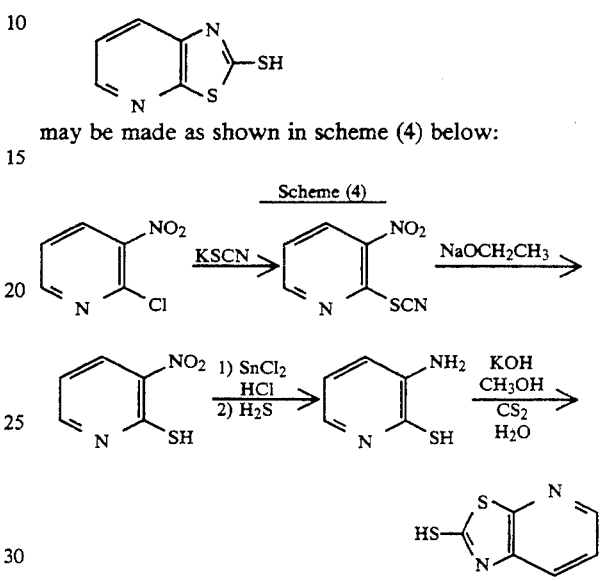

may be made as shown in scheme (4) below:

In the above scheme, 2-chloro-3-nitropyridine is treated with potassium isothiocyanate to provide 2-isocyanato-3-nitropyridine, which is in turn hydrolyzed to provide 2-mercapto-3-nitropyridine. The -nitro intermediate is then reduced by treatment with $SnCl_2$/HCl to provide 2-mercapto-3-amino pyridine. The desired pyridinothiazolothio mercaptan is then prepared by base catalyzed condensation with $CS_2$ (KOH/$CH_3OH$/$CS_2$/$H_2O$).

Examples of compounds falling within the scope of formula 1 are set forth in the table below:

TABLE 1

| R | A | A' (independently) |
|---|---|---|
| methyl | H | H |
| ethyl | H | H |
| propyl | H | H |
| butyl | H | H |
| pentyl | H | H |
| hexyl | H | H |
| isopropyl | H | H |
| isobutyl | H | H |
| t-butyl | H | H |
| isopentyl | H | H |
| isohexyl | H | H |
| fluoromethyl | H | H |
| 1-fluoroethyl-2-yl | H | H |
| 1-fluoroprop-3-yl | H | H |
| 1-fluoro-but-4-yl | H | H |
| 1-fluoro-hex-5-yl | H | H |
| chloromethyl | H | H |

TABLE 1-continued

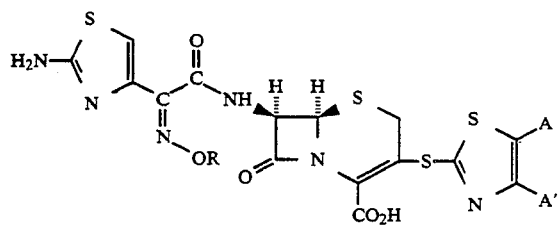

| R | A and A' together forming |
|---|---|
| 1-chloroeth-2-yl | H  H |
| 1-chloroprop-3-yl | H  H |
| 1-chlorobut-4-yl | H  H |
| bromomethyl | H  H |
| 1-bromoeth-2-yl | H  H |
| 1-bromoprop-3-yl | H  H |
| 1-bromobut-4-yl | H  H |
| vinyl | H  H |
| 1-propene-2-yl | H  H |
| 1-butene-4-yl | H  H |
| 1-pentene-5-yl | H  H |
| 1-hexane-6-yl | H  H |
| cyclopropyl | H  H |
| cyclobutyl | H  H |
| cyclopentyl | H  H |
| cyclohexyl | H  H |
| methyl | NO₂  H |
| ethyl | NO₂  H |
| propyl | NO₂  H |
| butyl | NO₂  H |
| pentyl | NO₂  H |
| hexyl | NO₂  H |
| isopropyl | NO₂  H |
| isobutyl | NO₂  H |
| t-butyl | NO₂  H |
| isopentyl | NO₂  H |
| isohexyl | NO₂  H |
| fluoromethyl | NO₂  H |
| 1-fluoroethyl-2-yl | NO₂  H |
| 1-fluoroprop-3-yl | NO₂  H |
| 1-fluoro-but-4-yl | NO₂  H |
| 1-fluoro-hex-5-yl | NO₂  H |
| chloromethyl | NO₂  H |
| 1-chloroeth-2-yl | NO₂  H |
| 1-chloroprop-3-yl | NO₂  H |
| 1-chlorobut-4-yl | NO₂  H |
| bromomethyl | NO₂  H |
| 1-bromoeth-2-yl | NO₂  H |
| 1-bromoprop-3-yl | NO₂  H |
| 1-bromobut-4-yl | NO₂  H |
| vinyl | NO₂  H |
| 1-propene-2-yl | NO₂  H |
| 1-butene-4-yl | NO₂  H |
| 1-pentene-5-yl | NO₂  H |
| 1-hexane-6-yl | NO₂  H |
| cyclopropyl | NO₂  H |
| cyclobutyl | NO₂  H |
| cyclopentyl | NO₂  H |
| cyclohexyl | NO₂  H |
| methyl | NH₂  H |
| ethyl | NH₂  H |
| propyl | NH₂  H |
| butyl | NH₂  H |
| pentyl | NH₂  H |
| hexyl | NH₂  H |
| isopropyl | NH₂  H |
| isobutyl | NH₂  H |
| t-butyl | NH₂  H |
| isopentyl | NH₂  H |
| isohexyl | NH₂  H |
| fluoromethyl | NH₂  H |
| 1-fluoroethyl-2-yl | NH₂  H |
| 1-fluoroprop-3-yl | NH₂  H |
| 1-fluoro-but-4-yl | NH₂  H |
| 1-fluoro-hex-5-yl | NH₂  H |
| chloromethyl | NH₂  H |
| 1-chloroeth-2-yl | NH₂  H |
| 1-chloroprop-3-yl | NH₂  H |
| 1-chlorobut-4-yl | NH₂  H |
| bromomethyl | NH₂  H |
| 1-bromoeth-2-yl | NH₂  H |
| 1-bromoprop-3-yl | NH₂  H |
| 1-bromobut-4-yl | NH₂  H |
| vinyl | NH₂  H |
| 1-propene-2-yl | NH₂  H |
| 1-butene-4-yl | NH₂  H |
| 1-pentene-5-yl | NH₂  H |
| 1-hexane-6-yl | NH₂  H |
| cyclopropyl | NH₂  H |
| cyclobutyl | NH₂  H |
| cyclopentyl | NH₂  H |
| cyclohexyl | NH₂  H |
| methyl | CH₃  H |
| ethyl | CH₃  H |
| propyl | CH₃  H |
| butyl | CH₃  H |
| pentyl | CH₃  H |
| hexyl | CH₃  H |
| isopropyl | CH₃  H |
| isobutyl | CH₃  H |
| t-butyl | CH₃  H |
| isopentyl | CH₃  H |
| isohexyl | CH₃  H |
| fluoromethyl | CH₃  H |
| 1-fluoroethyl-2-yl | CH₃  H |
| 1-fluoroprop-3-yl | CH₃  H |
| 1-fluoro-but-4-yl | CH₃  H |
| 1-fluoro-hex-5-yl | CH₃  H |
| chloromethyl | CH₃  H |
| 1-chloroeth-2-yl | CH₃  H |
| 1-chloroprop-3-yl | CH₃  H |
| 1-chlorobut-4-yl | CH₃  H |
| bromomethyl | CH₃  H |
| 1-bromoeth-2-yl | CH₃  H |
| 1-bromoprop-3-yl | CH₃  H |
| 1-bromobut-4-yl | CH₃  H |
| vinyl | CH₃  H |
| 1-propene-2-yl | CH₃  H |
| 1-butene-4-yl | CH₃  H |
| 1-pentene-5-yl | CH₃  H |
| 1-hexane-6-yl | CH₃  H |
| cyclopropyl | CH₃  H |
| cyclobutyl | CH₃  H |
| cyclopentyl | CH₃  H |
| cyclohexyl | CH₃  H |

| R | A and A' together forming |
|---|---|
| methyl | 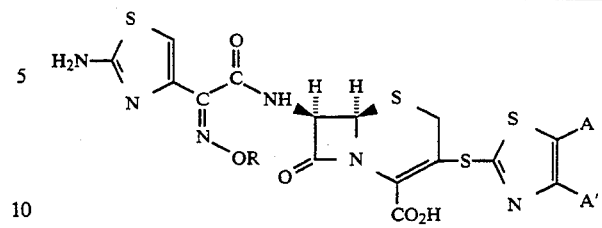 |
| ethyl | |
| propyl | |
| butyl | |
| pentyl | |
| hexyl | |
| isopropyl | |
| isobutyl | |
| t-butyl | |
| isopentyl | |
| isohexyl | |
| fluoromethyl | |
| 1-fluoroethyl-2-yl | |
| 1-fluoroprop-3-yl | |
| 1-fluoro-but-4-yl | |
| 1-fluoro-hex-5-yl | |
| chloromethyl | |
| 1-chloroeth-2-yl | |
| 1-chloroprop-3-yl | |
| 1-chlorobut-4-yl | |
| bromomethyl | |
| 1-bromoeth-2-yl | |
| 1-bromoprop-3-yl | |
| 1-bromobut-4-yl | |
| vinyl | |

TABLE 1-continued

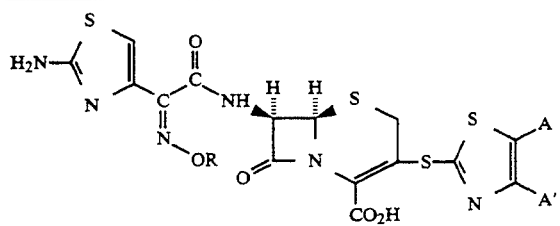

| | |
|---|---|
| 1-propene-2-yl | |
| 1-butene-4-yl | |
| 1-pentene-5-yl | |
| 1-hexane-6-yl | |
| cyclopropyl | |
| cyclobutyl | |
| cyclopentyl | |
| cyclohexyl | |
| methyl | |
| ethyl | 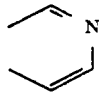 |
| propyl | |
| butyl | |
| pentyl | |
| hexyl | |
| isopropyl | |
| isobutyl | |
| t-butyl | |
| isopentyl | |
| isohexyl | |
| fluoromethyl | |
| 1-fluoroethyl-2-yl | |
| 1-fluoroprop-3-yl | |
| 1-fluoro-but-4-yl | |
| 1-fluoro-hex-5-yl | |
| chloromethyl | |
| 1-chloroprop-3-yl | |
| 1-chlorobut-4-yl | |
| bromomethyl | |
| 1-bromoeth-2-yl | |
| 1-bromoprop-3-yl | |
| 1-bromobut-4-yl | |
| vinyl | |
| 1-propene-2-yl | |
| 1-butene-4-yl | |
| 1-pentene-5-yl | |
| 1-hexane-6-yl | |
| cyclopropyl | |
| cyclobutyl | |
| cyclopentyl | |
| cyclohexyl | |
| methyl | |
| ethyl | 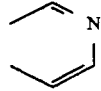 |
| propyl | |
| butyl | |
| pentyl | |
| hexyl | |
| isopropyl | |
| isobutyl | |
| t-butyl | |
| isopentyl | |
| isohexyl | |
| fluoromethyl | |
| 1-fluoroethyl-2-yl | |
| 1-fluoroprop-3-yl | |
| 1-fluoro-but-4-yl | |
| 1-fluoro-hex-5-yl | |
| chloromethyl | |
| 1-chloroeth-2-yl | |
| 1-chloroprop-3-yl | |
| 1-chlorobut-4-yl | |
| bromomethyl | |
| 1-bromoeth-2-yl | |
| 1-bromoprop-3-yl | |
| 1-bromobut-4-yl | |
| vinyl | |
| 1-propene-2-yl | |
| 1-butene-4-yl | |
| 1-pentene-5-yl | |
| 1-hexane-6-yl | |
| cyclopropyl | |
| cyclobutyl | |

TABLE 1-continued

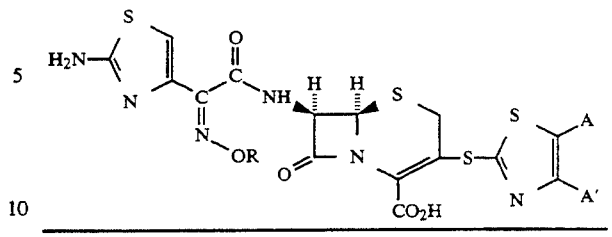

| R | A and A' taken together forming |
|---|---|
| cyclopentyl | |
| cyclohexyl | |
| methyl | |
| ethyl | |
| propyl | |
| butyl |  |
| pentyl | |
| hexyl | |
| isopropyl | |
| isobutyl | |
| t-butyl | |
| isopentyl | |
| isohexyl | |
| fluoromethyl | |
| 1-fluoroethyl-2-yl | |
| 1-fluoroprop-3-yl | |
| 1-fluoro-but-4-yl | |
| 1-fluoro-hex-5-yl | |
| chloromethyl | |
| 1-chloroeth-2-yl | |
| 1-chloroprop-3-yl | |
| 1-chlorobut-4-yl | |
| bromomethyl | |
| 1-bromoeth-2-yl | |
| 1-bromoprop-3-yl | |
| 1-bromobut-4-yl | |
| vinyl | |
| 1-propene-2-yl | |
| 1-butene-4-yl | |
| 1-pentene-5-yl | |
| 1-hexane-6-yl | |
| cyclopropyl | |
| cyclobutyl | |
| cyclopentyl | |
| cyclohexyl | |

In the above Formula (1), R is preferably $C_1-C_6$ alkyl or $C_1-C_6$ haloalkyl. A preferred $C_1-C_6$ alkyl group is methyl. A preferred $C_1-C_6$ haloalkyl group is fluoro-$C_1-C_6$ alkyl. A further preferred fluoro-$C_1-C_6$ alkyl group is the 2-fluoroeth-1-yl group.

In the above Formula (1), it is preferred that A and A' are taken together to form a group of the formulae

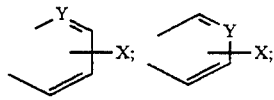

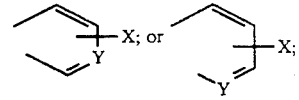

It is further preferred that Y is nitrogen and A and A' are taken together to form a group o the formula

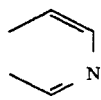

for example, providing a compound of the formula

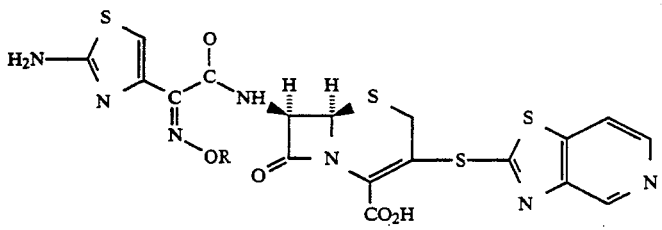

or a pharmaceutically acceptable salt thereof. Two further preferred compounds of the above formula are where R is methyl or 2-fluoroeth-1-yl.

This invention also provides a method for treating infectious diseases in man and other animals and pharmaceutical formulations suitable for administration in the treatment method. The therapeutic method of this invention comprises administering to man or other animals an antibiotically effective non-toxic dose of a compound represented by Formula (1) or a pharmaceutically acceptable salt thereof.

An antibiotically effective amount is an amount between about 25 mg and about 2 grams. The compound, salt or ester may be administered in a single dose or in multiple doses throughout the day. Treatment may continue for a week to ten days or longer depending upon the duration of the infection. The particular dose and regimen can depend on such factors as the weight and age of the patient, the particular causative organism, the severity of the infection, the general health of the patient, and the tolerance of the individual to the antibiotic.

The cephalosporin may be administered parenterally, subcutaneously or rectally. As with other β-lactam antibiotics, the method of this invention may be used prophylactically to prevent infections after exposure or before possible exposure, e.g., preoperatively. The antibiotic may be administered by conventional methods, e.g., by syringe or by intravenous drip.

The pharmaceutically-acceptable salts as noted above can be useful forms of the antibiotics for preparing antibiotic formulations.

The pharmaceutical formulations of the invention comprise an antibiotically effective non-toxic amount of a compound represented by Formula (1) or a pharmaceutically acceptable non-toxic salt thereof, and a pharmaceutically acceptable carrier.

Parenteral formulations of the antibacterial agent for injection are formulated with Water-for-Injection, Ringer's solution, physiological saline or glucose solution. The antibiotic also may be administered in an intravenous fluid by the drip method.

For parenteral use the antibacterial agent of Formula (1) or a pharmaceutically acceptable salt thereof, can be made up preferably in dry crystalline powder form or as a lyophilized powder and filled into vials. Such vials may contain between about 100 mg and about 2 grams of antibiotic per vial.

As a further aspect of the present invention, there are provided novel intermediates of Formula (2):

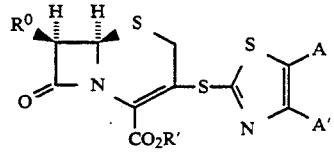

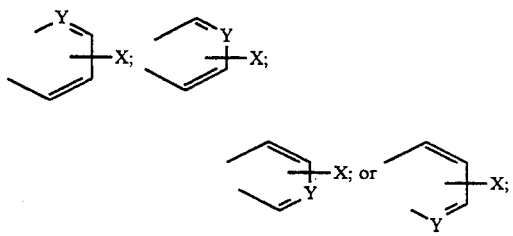

wherein $R^o$ is amino or a a protected amino group; R' is hydrogen or a carboxy-protecting group; and A and A' are independently hydrogen, $C_1$-$C_6$ alkyl, phenyl, nitro, amino, a 5-6 membered heterocycle containing nitrogen or sulfur, or $C_1$-$C_6$ alkoxy; or A and $A^1$ taken together form a group of the formulae wherein X is hydrogen, $C_1$-$C_6$ alkyl, $C_1$-$C_6$ alkoxy, $C_1$-$C_6$ alkoxycarbonyl, amino, nitro, or carboxy, and Y is nitrogen or carbon.

In Formula (2), the term "carboxy-protecting group" refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-di-methoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsil t-butyldimethylsilyl, phenacyl, 2,2,2-trichloroethyl, β-(trimethylsilyl)ethyl, β-(di(n-butyl)methyldilyl)-ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed herein.) Preferred carboxylic acid protecting groups are the allyl, the benzhydryl, and the p-nitro benzyl groups. Similar carboxy-protecting groups used in the cephalosporin, penicillin and peptide arts can also be used to protect a carboxy group. Further examples of these groups are found in E. Haslam, "Protective Groups in Organic Chemistry", J. G. W. McOmie, Ed., Plenum Press, New York, N. Y., 1973, Chapter 5, and T. W. Greene, "Protective Groups in Organic Synthesis", John Wiley and Sons, New York, N. Y., 1981, Chapter 5.

The term "protected amino group" as used in Formula (2) refers to an amino group substituted by a group commonly employed to block or protect the amino functionality while reacting other functional groups on the compound. Examples of such amino-protecting groups include the formyl group, the trityl group, the t-butoxycarbonyl group, the phthalimido group, the phenoxyacetyl, trichloroacetyl group, the chloroacetyl, bromoacetyl and iodoacetyl groups, urethane-type blocking groups such as benzyloxycarbonyl, 4-phenylbenzyloxycarbonyl, 2-methlbenzyloxycarbonyl, 4-methoxybenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenxyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(P-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methycyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)-prop-1-enyloxycarbonyl, 5-benzisoxalyl-methoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, iso-bornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the allyloxycarbonyl, the phenoxyacetyl, the t-butoxycarbonyl, and the trityl groups. Similar amino-protecting groups used in the cephalosporin, pencillin and peptide art are also embraced by the above terms. Further examples of groups referred to by the above terms are described by J. W. Barton, "Protective Groups in Organic Chemistry", J. G. W. McOmie, Ed., Plenum Press, New York, N. Y., 1973, Chapter 2, and T. W. Greene, "Protective Groups in Organic Synthesis", John Wiley and Sons, New York, N.Y., 1981, Chapter 7.

In Formula (2), it is preferred that A and A' are taken together to form a group of the formulae

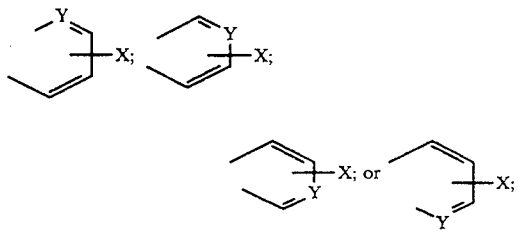

It is especially preferred that A and A' are taken together to form a group of the formula

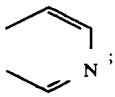

thus providing a compound of the formula

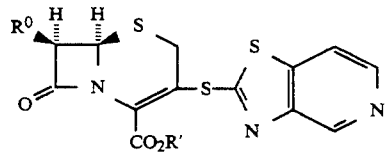

The compounds of formula (2) are useful as intermediates in the preparation of the antibacterial agents of Formula(1) above. The compounds of formula (2) may be prepared by the methodology as taught in scheme (1) above displacing the 3-triflate moiety with the desired thiol of the formula

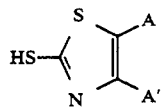

utilizing a 7-protected amino nucleus.

The final products (1) may then be prepared from intermediates of formula (2) by deprotection of the 7-amino function if necessary, followed by acylation with a desired acyl group, and subsequent amino/carboxy protecting group removal.

The following Experimental Section provides further examples of the various aspects of the present invention but is not to be construed as limiting the scope therefore.

Experimental Section

Preparation 1

7β-amino-3-chloro-3-cephem-4-carboxylic acid

The title compound may be prepared by the method of Chauvette, U.S. Pat. No. 4,064,343, incorporated herein by reference.

Preparation 2

3-(t-butyloxycarbonyl)amino pyridine

A 76.13 g (0.81 mol) sample of 3-aminopyridine was dissolved in 500 ml of water, along with 150 ml of t-butanol and 34 g (0.85 mol) of NaOH, cooled in an ice bath, and treated with 200 g (0.92 mol) of di-t-butyldicarbonate. After about 2.5 days, another 100 g of di-t- butyl dicarbonate was added. The reaction mixture was then poured into an ethyl acetate/water mixture. The organic phase was separated and the remaining aqueous phase was extracted with ethyl acetate. The combined organic portions were dried over anhydrous sodium sulfate, concentrated in vacuo, and purified via flash chromatography to provide 97 g (80%) of the title compound.

$^1$H NMR: (300 MHz, CDCl$_3$) δ8.43(d, J=1.5Hz, 1H), 8.26 (d, J=3Hz, 1H), 7.97 (br d, J=6Hz, 1H), 7.24–7.20 (m, 1H), 6.81 (br s, 1H), 1.51 (s, 9H).

IR: (KBr, cm ) 3167, 2986, 1716, 1598, 1545, 1407, 1566, 1288, 1233, 1154, 1017

MS: FDMS m/e 195 (M+)

UV: (ethanol) λ=281 nm (ε=3350), λ=235 nm (ε=15200),

Preparation 3

3-(t-Butyloxycarbonyl)amino-4-mercaptopyridine

A 10 g (51.5 mmol) sample of 3-(t-butyloxycarbonyl)amino pyridine was dissolved in 110 ml of tetrahydrofuran and cooled to −78° C. under nitrogen. An 80 ml (128 mmol, 1.6 M in hexanes) sample of n-butyllithium was then added in two portions. The reaction mixture was then placed in an acetone/ice bath to allow the resulting solid to dissolve. After about 2 hours, the reaction mixture was then cooled to −78° C. and treated with 2 g (7.8 mmol) of elemental sulfur. After about ½ hour, the reaction mixture was allowed to warm to room temperature and was quenched with a saturated NH$_4$Cl solution. Work-up and flash chromatography (50% Hexane/ethyl acetate) provided 5.24 g (45%) of the title compound.

m.p.=170°–171° C. (dec.)

$^1$H NMR: (300 MHz, DMSO-d$_6$) δ12.88 (br s, 1H), 8.95 (s, 1H), 8.45 (br s, 1H), 7.62 (br d, J=3Hz, 1H), 7.44 (d, J=3Hz, 1H), 1.49 (s, 9H).

IR: (KBr, cm$^{-1}$) 3239, 2978, 2885, 2741, 1721, 1608, 1530, 1492, 1436, 1384, 1213, 1161, 1085

MS: FDMS m/e 227 (M+)

UV: (ethanol) λ=345nm (ε=19600 ), λ=259nm (ε=10200), λ=224nm (s=17200).

Preparation 4

3-Amino-4-mercapto-pyridine hydrochloride

A 13.78 g (0.06 mol) sample of 3-(t-butyloxycarbonyl)amino-4-mercapto pyridine was dissolved with acetic acid (250 mL) and added to an ice cold solution of ∼3N HCl in acetic acid which had been made by bubbling HCl$_{(g)}$ through glacial acetic acid (100 mL). After about four hours the resulting solid was filtered, washed with diethylether and dried in vacuo to yield 10.4 g (∼100%) of the title compound. m.p.: >200° C.

$^1$H NMR: (300 MHz, DMSO-d$_6$) δ8.17 (s, 1H), 7.99 (d, J=3 Hz, 1H), 7.81 (d, J=3 Hz, 1H), 5.60–4.00 (br, 4H).

IR: (KBr, cm$^{-1}$) 3184, 3054, 2848, 1639, 1586, 1482, 1442, 1134, 1123

MS: FDMS m/e 126 (M-36)

UV: (ethanol) λ=355 nm, (ε=13900), λ=264nm, (ε=6830), λ=223nm, (s=13100),

Preparation 5

2-Mercapto-5-pyridinothiazole

A 13 g (0.198 mol) sample of potassium hydroxide was dissolved in 32 ml of water and 154 ml of methanol. This solution was then treated with 3.8 ml (0.063 mol) of CS$_2$, followed by a 10.4 g (0.06 mol) sample of 3-amino-4-mercaptopyridine hydrochloride. After stirring at reflux overnight, the reaction mixture was treated with decolorizing carbon and filtered through Hyflo Super Cel™. The filtrate was acidified with acetic acid causing a solid to form. The resulting solid was dried in vacuo at 50° C. for about 3 hours and at room temperature for about 2.5 days to provide 8.19 g (81%) of the title compound.

m.p. >310 dec.

$^1$H NMR: (300 MHz, DMSO-d$_6$)δ14.03 (br s, 1H), 8.46 (S, 1H), 8.33 (d, J=6Hz, 1H) 7.75 (d, J=6Hz, 1H).

IR: (KBr cm$^{-1}$) 3440(br), 2650(br), 2510(br), 1528, 1457, 1305, 1294, 1265, 12S6, 1039, 1024, 815

MS: EI MS m/e 168 (M.)

Preparation 6

2-isothiocyanato-3-nitro pyridine

A 10 g sample of 2-chloro-3-nitropyridine, an 8 g sample of potassium isothiocyanate, and 75 ml of acetic acid were combined and refluxed for 2 h. The reaction mixture was then cooled and poured into 400 ml of ice/H$_2$O. The resulting solid was washed with water, redissolved in ethyl acetate and washed (4×) with water. The ethyl acetate solution was then treated with activated carbon, dried over anhydrous Na$_2$SO$_4$, filtered and evaporated to dryness to provide 3.72 g of the title compound. m.p.=115°–118° C.

$^1$H NMR: (300 MHz, CDCl$_3$)δ8.62 (m, 1H), 8.22 (d, J=6Hz, 1H), 7.46 (m, 1H).

Preparation 7

2-Mercapto-3-nitropyridine

A 50 ml sample of ethanol was treated with 612 mg of sodium at reduced temperature (ice bath) under substantially anhydrous conditions. The reaction mixture was then treated with a 3.6 g (0.02 mol) sample (in portions) of the title compound of preparation 6. The reaction was stirred for 2 h, diluted with 250 ml of H$_2$O and evaporated in vacuo. The resulting solid was filtered off and discarded. The solution was then acidified with acetic acid to pH=4.5 and yellowish-red crystals formed. The title compound was filtered off, washed with water and dried under vacuum over a dessicant to provide 1.1 g (m.p.=185°–7° C. (dec.))

$^1$H NMR: (300 MHz, CDCl$_3$) δ8.09 (d, J=7Hz, 1H), 7.89 (d, J=7Hz, 1H), 6.84 (dd, J=6, 3Hz, 1H).

IR: (KBr cm$^{-1}$) 3119, 2872, 1611, 1577, 1527, 1349, 1330, 1240, 1141.

MS: EI MS m/e 126 (M+).

Preparation 8

2-Mercapto-3-aminopyridine

A 100 ml sample of concentrated HCL(aq) was cooled in an ice bath and treated with 100 g (0.53 mol) of SnCl$_2$. The reaction mixture was then treated with a 14 g (0.11 mol) sample of the title compound from preparation 7, in portions, and stirred for 3 hours.

The reaction mixture was then evaporated to a solid, dissolved in 1 L H$_2$O, and treated with H$_2$S(g) for 30 min., while heating over a steam bath. The resulting solid was filtered off, washed with hot H$_2$O and discarded. The combined aqueous portions were evaporated to afford a solid. The resulting solid was digested (2×) with hot concentrated NH$_4$OH. The resulting solid was filtered and discarded and the NH$_4$OH solution was evaporated to afford a wet solid, which was, in turn, mobilized in H₂O. The resulting yellow/green title compound was filtered, washed with H₂O, and dried in vacuo at 40° over dessicant.

Yield=4.20 g (30%)
m.p.=127°-128° C

¹H NMR: 300 MHz, CDCl₃/DMSO-d₆)δ6 6.91 (m, 1H), 6.65 (d, J=5Hz, 1H), 6.46 (m, 1H), 5.03 (s, 2H).

Preparation 9

2-Mercapto-7-pyridinothiazole

A 2.8 g (85%) sample of KOH was dissolved in 16 ml of HzO and 50 ml of methanol. A 2.6 g sample of CS₂ was then added and washed in with 30 ml of methanol. A 4 g (23.8 mmol) sample of 2-mercapato-3-aminopyridine was added and the reaction mixture refluxed overnight. After cooling, the reaction mixture was treated with activated carbon and filtered through Super Cel ™, while washing the Super Cel ™ pad with a small amount of methanol. The solution was then acidified to pH=5.5 with acetic acid. The title compound precipitated from this solution as a yellowish solid and was dried at 60° C. over a dessicator. Yield=3.29 g m.p.=285°-287° C. (dec)

¹H NMR: (300 MHz, DMSO-d₆)δ8.38 (dd, J=3, 1.5 Hz, 1H), 7.61 (dd, J=4, 1.5 Hz, 1H), 7.43 (dd, J=5, 3Hz, 1H), 3.33 (br s, 1H)

IR: (KBr cm⁻¹) 3040, 2700, 2540, 1597, 1523, 1399, 1311, 1302, 1274, 1132, 876.

MS: EI MS m/e 169 (m+1)

Preparation 10

Ethyl(2-(triphenylmethyl)-aminothiazol-4-yl)-2-bromoeth-1-yl-oximinoacetate

A 9.88 g (0.02 mol) sample of ethyl-(2-(triphenylmethyl)aminothiazol-4-yl)oximinoacetate was dissolved in 20 ml of N,N′-dimethylformamide and treated with 8.28 g (0.06 mol) of powdered potassium carbonate. After ½ h of stirring, 17.3 ml of 1,2-dibromoethane was added and the reaction mixture was stirred overnight under argon.

The reaction mixture was then poured into 100 mo of CH₂Cl₂/200 ml H₂O. The aqueous layer was again extracted with CH₂Cl₂. The combined CH₂Cl₂ phase was washed with H₂O and brine, dried over anhydrous MgSO₄, filtered, and evaporated in vacuo to provide an oil. Liquid chromatography (25% hexane/CH₂Cl₃) provided 7.16 g (63.4%) of the title compound.

m.p.=55° C.

¹H NMR: (300 MHz, CDCl₃δ7.32 (s, 15H), 6.52 (s, 1H), 4.55–4.46 (m, 2H), 4.38 (q, J=4 Hz, 2H), 3 63–3.53 (m, 2H), 1.37 (t, J=4 Hz, 3H)

Elem. Anal: calc'd: C: 59.58; H: 4.64; N: 7.44, obs'd: C: 59.36; H: 4.61; N: 7.18.

Preparation 11

Ethyl(2-(triphenylmethyl)aminothiazol-4-yl)-2-fluroeth-1-yl-oximino acetate

The title compound was prepared in a manner analogous to that of Preparation 10, substituting 1-bromo-2-fluoroethane as the alkylating agent.

Yield=3.3 g

¹H NMR: (300 MHz, DMSO-d₆)δ8.77 (s, 1H), 7.39–7.12 (m, 15H), 6.92 (s, 1H), 4.60 (t, J=3Hz, 1H), 4.44 (t, J=3Hz, 1H), 4.26 (t, J=3Hz, 1H), 4.16 (t, J=3Hz, 1H), 4.16 (t, J=3Hz, 1H), 3.90 (q, J=4Hz, 2H), 1.06 (t, J=4Hz, 3H).

Preparation 12

(2-(Triphenylmethyl)aminothiazol-4-yl)-2-fluoroeth-1-yl-oximinacetine acid

A 2.5 g (5 mmol) sample of the title compound of preparation 11 was dissolved in 20 ml of ethanol and 5 ml (10 mmol) of 2N NaOH. After stirring for 2 h at 50° C., the sodium salt of the acid crystallized. This solid was slurried in H₂O/CHCl₃ and acidified with 1N HCl. The aqueous layer was extracted again with CHCl₃ and the combined CHCl₃ phase was washed with water, brine, and dried over anhydeous Na₂SO₄. The CHCl₃ phase was then evaporated in vacuo to provide 1.52 g (63.9%) of the title compound as a foam.

m.p.=125.33° C. (dec)

¹H NMR: (300 MHz, CDCl₃)δ9.70 (br s, 1H), 7.30–7.22 (m, 15H), 6.52 (s, 1H), 4.65 (t, J=3Hz, 1H), 4.49 (t, J=3Hz, 1H), 4.37 (t, J=3Hz, 1H), 4.27 (t, J=3Hz, 1H)

IR: (CDCl₃, cm¹) 3000, 1735, 1592, 1529, 1449, 1186, 1070, 1035

Example 1

7β-[(2-aminothiazol-4-yl)-(Z)-methoximino-acetyl]amino-3-[2-(5-pyridinothiazolothio)]-3-cephem-4-carboxylic acid

A.

7β-[(2-(triphenylmethyl)aminothiazol-4-yl-(Z)-methoximinoacetyl]amino-3-chloro-3-cephem-4-carboxylic acid A 39.8 g (0.17 mol) sample of 7β-amino-3-chloro-3-cephem-4-carboxylic acid was suspended in 800 of N,N′-dimethylformamide and treated with 100 g (0.49 mol) of bis(dimethylsilyl)urea and heated to about 50°–65° C. for about 1 hour.

In another reaction vessel, a 100 g (0.21 mol) sample of 2-(triphenylmethyl)aminothiazol-4-yl-(Z)-methoximinoacetic acid was dissolved in 800 ml of N,N′-dimethylformamide and cooled in an ice/acetone bath. The reaction mixture was then treated with 23 ml (0.21 mol) of N-methylmorpholine followed by 25 g (0.20 mol) of oxalyl chloride.

In the first reaction vessel above, the reaction mixture was treated with 32 ml (0.40 mol) of pyridine and transferred via cannula to the second reaction vessel over 50 minutes.

The reaction mixture was then poured into about 2.5 L of ice/H₂O and the resulting solid air dried to provide 116 g of the title compound (3:1 Δ³:Δ² mixture).

¹H NMR: (300 MHz, DMSO-d₆)δ9.61 (d, J=9Hz, 1H), 8.83 (s, 1H×¼), 8.80 (s, 1H×¾), 7.46–7.10 (br m, 15H), 6.83 (s, 1H), 6.68 (s, 1H×¼), 5.72–5.66 (m, 1H×¾), 5.60–5.54 (m, 1H×¼), 5.23–5.17 (m, 1H×¼), 5.20 (d, J=5Hz, 1H×¾), 4.83 (s, 1H×¼), 3.80 (s, 3H), 3.79 (ABq, J=20Hz, 2H×¾).

B. Benzhydryl 7β-[2-(triphenylmethyl)aminothiazol-4-yl-(Z)-methoximinoacetyl]amino-3-chloro-3-cephem-4-carboxylate The material from part A, above, was dissolved in 500 ml of CH₃CN and treated with 10 g (XS) of diphenyldiazomethane and stirred at room temperature for about 2.5 days. The reaction mixture was then quenched with acetic acid and concentrated in vacuo, utilizing toluene to azeotrope excess acetic acid. Purification via flash chromatography (25% and 50% ethyl acetate/hexane) provided 15.46 g of a 2:1 ($\Delta^2/\Delta^3$) mixture.

$^1$H NMR: (300 MHz, DMSO-d$_6$)δ9.60 (d, 6Hz, 1H), 8.80 (s, 1H), 7.46–7.02 (br. m, 25H), 6.92 (s, 1H×⅓), 6.88 (s, 1H×⅔), 6.84 (s, 1H×⅔), 6.78 (s, 1H×⅔), 6.67 (s, 1H×⅓), 5.76–5.70 (m, 1H×⅓), 5.51–5.45 (m, 1H×⅔), 5.28–5.22 (m, 1H×⅔), 5.26 (s, 1H×⅓), 5.12 (d, J=4Hz, 1H×⅔), 3.79 (ABq, J=19Hz, 2H×⅓), 3.77 (s, 3H).

C. Benzhydryl 7β-[2-(triphenylmethyl)aminothiazol-4-yl-(Z)-methoximino]acetyl-3-[2-(5-pyridinothiazolothio)]-3-cephem-4-carboxylate A 92 mg (2.3 mmol; 60% in oil) sample of NaH was washed with hexanes and suspended in 50 ml of tetrahydrofuran and treated with a 390.9 mg (2.3 mmol) sample of 2-mercapto-5-pyridinothiazole and heated. This solution was transferred via cannula to a 5.7 g (2.3 mmol) sample of the compound prepared in part B, above, dissolved in 50 ml of tetrahydrofuran. The reaction mixture was then treated with 15 ml of 1N HCl and poured into an ethyl acetate/water mixture. The organic phase was washed with brine, dried over anhydrous Na$_2$SO$_4$, filtered and concentrated in vacuo. After column chromatography (75%–90% ethyl acetate/hexane), the pure $\Delta^3$ isomer crystallized out. (0.31 g, 34%).

$^1$H NMR: (300 MHz, DMSO-d$_6$)δ9.70 (d, J=9Hz, 1H), 9.10 (s, 1H), 8.79 (s, 1H), 8.47 (d, J=7Hz, 1H), 8.08 (d, J=7Hz, 1H), 7.38–7.03 (br m, 25H), 6.91 (s, 1H), 6.68 (s, 1H), 5.90–5.82 (m, 1H), 5.37 (d, J=8Hz, 1H), 3.83 (ABq, J=20Hz, 2H), 3.78 (s, 3H).

IR: (KBr, cm$^{-1}$) 3402 (br), 3030, 2938, 1786, 1738, 1695, 1522, 1496, 1371, 1278, 1223, 1044, 700.

MS: FABMS m/e 958 (m+)

OR: [α]$_D$= –133.33 degrees @ 589 nm, F5 mg/DMSO

Elem. Anal: calc'd: C: 63.93; H: 4.10; N: 10.23, obs'd: C: 64.19; H: 4.06: N: 10.43.

D. Deprotection to provide title compound

A 0.42 g (438 mmol) sample of the product from part C, above, was suspended with 7 ml of triethylsilane and 10 ml of CH$_2$Cl$_2$ and treated with 5 ml of trifuloroacetic acid and stirred at room temperature. The reaction mixture was then concentrated, in vacuo, utilizing toluene to azeotrope excess trifluoroacetic acid. The resulting residue was purified by reverse phase chromatography (10%–20% CH$_3$CN/H$_2$O).

$^1$H NMR: (300 MHz, DMSO-d$_6$)δ9.75 (d, J=9Hz, 1H), 9.18 (s, 1H), 8.49 (d, J=6Hz, 1H), 8.19 (d, J=6Hz, 1H), 7.21 (br s, 2H), 6.71 (s, 1H), 5.94 (dd, J=5Hz, 10Hz, 1H), 5.35 (d, J=6Hz, 1H), 3.88 (ABq, J=15Hz, 2H), 3.85 (s, 3H).

IR: (KBr, cm$^{-1}$) 3395, 1782, 1621, 1532, 1381, 1037.
MS: FABMS m/e 550 (m)
UV: (EtOH) λ=286 nm (E 22700), λ=231 nm (E 34200),
OR: 5 mg/DMSO [α]$_D$= –123.26 degrees @ 589 nm

Examples 2–5

Examples 2 through 5, which follow, were prepared in a manner essentially as described in Example 1, by utilizing different mercaptans of the formula

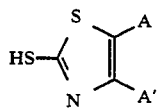

Example 2

7β-[(2-aminothiazol-4-yl)-(Z)-(2-fluoroeth-1-yl)-oximinoacetyl]amino-3-[2-(5-pyridinothiazolo)]thio-3-cephem-4-carboxylic acid $^1$H NMR: (300 MHz, DMSO-d$_6$):δ9.70 (d, 1H, J=10Hz); 9.03 (S, 1H); 8.39 (d, 1H, J=5Hz); 8.03 (d, 1H, J=5Hz); 7.20 (S, 2H); 6.72 (S, 1H); 5.73 (m, 1H); 5.19 (d, 1H, J=7Hz); 4.67 (t, 1H, J=5Hz); 4.55 (t, 1H, J=5Hz); 4.32 (t, 1H, J=5Hz); 4.22 (t, 1H, J=5Hz); 3.63 (ABq, 2H, J=18Hz)

IR: (KBr) 3420, 1774, 1668, 1663, 1653, 1617, 1534, 1388 cm$^{-1}$

MS: (FAB) m/e=604 (m+1)
UV: (EtOH) λ=288 nm (ε=21700); 232 nm (ε=31400)
OR: [α]°$_{DMSO}$= –89.22°

Example 3

7β-[(2-aminothiazol-4-yl)-(Z)-(2-fluoroeth-1-yl)-oximinoacetyl]amino-3-[2-(7-pyridinothiazolothio)]-3-cephem-4-carboxylic acid Yield=13% overall (22.8 mg)

$^1$H NMR: (300 MHz, DMSO-d$_6$)δ9.68 (d, 1H, J=10Hz); 8.25 (d, 1H, J=5Hz); 8.14 (d, 1H, J=10Hz); 7.45 (m, 1Hz); 7.20 (s, 2H); 6.72 (s, 1H); 5.70 (m, 1H); 5.20 (d, 1H, J=5Hz); 4.70 (t, 1H, J=5Hz); 4.53 (t, 1H, J=5Hz); 4.30 (t, 1H, J=5Hz); 4.20 (t, 1H, J=5Hz); 3.63 (ABq, 2H, J=15Hz).

MS: (FAB) m/e=604 (m+1)

Example 4

7β-(2-aminothiazol-4-yl)-(Z)-(2-fluoroeth-1-yl)-oximinoacetyl]amino-3-(thiazol-2-yl)thio-3-cephem-4-carboxylic acid Yield=63 mg (71%)

$^1$H NMR: (300 MHz, DMSO-d$_6$)δ9.67 (d, 1H, J=10Hz); 7.76 (s, 2H); 7.20 (s, 2H); 6.72 (s, 1H); 5.80–5.70 (m, 1H); 5.20 (d, 1H, J=5Hz); 4.66 (t, 1H, J=5Hz); 4.50 (t, 1H, J=5Hz); 4.28 (t, 1H, J=5Hz); 4.19 (t, 1H, J=5Hz); 3.50 (ABq, 2H, J=15Hz)

IR: (KBr) 3400, 1768, 1653, 1614, 1535, 1389, 1350, 1035 cm$^{-1}$

MS: (FAB) m/e=(m–1) 553
UV: (ethanol) λ=284 nm (ε=14900); 231 nm (ε=18100)

EXAMPLE 5

7β-[2-aminothiazol-b 4-yl-(Z)-(2-fluoroeth-1-yl)-oximinoacetyl]amino-3-[(benzothiazol-2-yl)thio]-3-cephem-4-carboxylic acid, sodium salt $^1$H NMR: (300 MHz, DMSO-d$_6$): δ9.67 (d, 1H, J=10Hz); 7.92 (d, 1H, J=10Hz); 7.78 (d, 1H, J=10Hz); 7.43–7.26 (m, 2H); 7.20 (s, 2H); 6.73 (s, 1H); 5.66 (m, 1H); 5.15 (d, 1H, J=5Hz); 4.70 (t, 1H, J=5Hz); 4.53 (t, 1H, J=5Hz); 4.30 (t, 1H, J=5Hz); 4.20 (t, 1H, J=5Hz); 3.64 (ABq, 2H, J=15Hz)

MS: (FAB) m/e=603 (m+1)

1. A compound of the formula
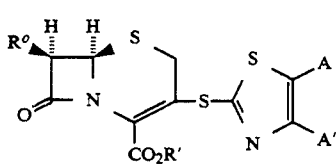
wherein R⁰ is amino or protected amino; R¹ is hydrogen or a carboxy-protecting group; and A and A' taken together form a group of the formula
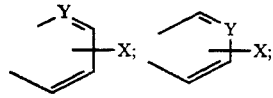
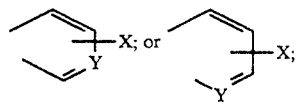
wherein X is hydrogen, $C_1$–$C_6$ alkyl, $C_1$–$C_6$ alkoxy, $C_1$–$C_6$ alkoxycarbonyl, amino, nitro, carboxy, and Y is nitrogen.
2. The compound as recited in claim 1 wherein A and A' form group of the formula

I claim: